(12) United States Patent
Kim et al.

(10) Patent No.: US 8,046,054 B2
(45) Date of Patent: Oct. 25, 2011

(54) BI-PLANAR FLUOROSCOPY GUIDED ROBOT SYSTEM FOR MINIMALLY INVASIVE SURGERY AND THE CONTROL METHOD THEREOF

(75) Inventors: Young Soo Kim, Seoul (KR); Byung-Ju Yi, Busjepm-si (KR); Jong-Il Park, Seoul (KR); Sung-min Kim, Seoul (KR); Se-Min Oh, Gyeonggi-do (KR)

(73) Assignee: Industry-University Cooperation Foundation, HANYANG UNIVERSITY, a university foundation of Seoul, Seoul (KR)

( * ) Notice: Subject to any disclaimer, the term of this patent is extended or adjusted under 35 U.S.C. 154(b) by 1094 days.

(21) Appl. No.: 11/530,653

(22) Filed: Sep. 11, 2006

(65) Prior Publication Data

US 2010/0249800 A1    Sep. 30, 2010

(30) Foreign Application Priority Data

Jan. 23, 2006 (KR) .......................... 10-2006-006851

(51) Int. Cl.
*A61B 5/05* (2006.01)
(52) U.S. Cl. ............... 600/427; 600/424; 901/15; 378/4
(58) Field of Classification Search ............... 600/427, 600/424; 901/15; 378/4
See application file for complete search history.

(56) References Cited

U.S. PATENT DOCUMENTS

| | | | | | |
|---|---|---|---|---|---|
| 5,784,542 | A | * | 7/1998 | Ohm et al. | 700/260 |
| 6,024,695 | A | * | 2/2000 | Taylor et al. | 600/102 |
| 6,149,592 | A | * | 11/2000 | Yanof et al. | 600/427 |
| 6,546,279 | B1 | * | 4/2003 | Bova et al. | 600/429 |
| 2003/0014034 | A1 | * | 1/2003 | Strobel | 604/407 |
| 2006/0098851 | A1 | * | 5/2006 | Shoham et al. | 382/128 |

OTHER PUBLICATIONS

"A Robot with Improved Absolute Positioning Accuracy for CT Guided Stereotactic Brain Surgery", Y.S. Kwoh, J. Hou, E.A. Jonckheere, and S. Hayati, IEEE, pp. 153-160, 1988.*

* cited by examiner

*Primary Examiner* — Tse Chen
*Assistant Examiner* — Jason Ip
(74) *Attorney, Agent, or Firm* — Schmeiser, Olsen & Watts LLP

(57) ABSTRACT

Disclosed is a computer-integrated surgery aid system for minimally invasive surgery and a method for controlling the same. The system includes a surgery planning system for creating three-dimensional information from two-dimensional images obtained by means of biplanar fluoroscopy so that spinal surgery can be planned according to the image information and a scalar-type 6 degree-of-freedom surgery aid robot adapted to be either driven automatically or operated manually.

10 Claims, 11 Drawing Sheets

BI-PLANAR FLUOROSCOPY GUIDED ROBOT SYSTEM FOR MINIMALLY INVASIVE SURGERY AND THE CONTROL METHOD THEREOF

BACKGROUND OF THE INVENTION

1. Field of the Invention

The present invention relates to a method for measuring three-dimensional surgical space. More particularly, the present invention relates to a computer-integrated surgery aid system for minimally invasive surgery including a surgery planning system for creating three-dimensional information from two-dimensional images obtained by means of biplanar fluoroscopy so that spinal surgery (e.g. spinal pedicle screw surgery, spinal endoscopy surgery, vertebroplasty, biopsy, scoliosis correction) can be planned according to the information and a scalar-type 6 degree-of-freedom surgery aid robot adapted to be either driven automatically or operated manually, as well as a method for controlling the same.

2. Description of the Prior Art

Conventional methods for spinal surgery are based on two-dimensional imaging in the lateral direction by using a C-Arm (unilateral X-ray) and require full incision of the surgical part. Therefore, they have the problem of a long surgery time and a long recovery time after surgery.

During surgery, holes are made where spinal pedicle screws are to be placed, and paths are established so that the screws are positioned. Then, the screws are inserted and connected to one another, and the screws are finally fastened by connecting rods.

The entire procedure of the conventional methods, from making holes to inserting screws, is based on the surgeon's senses, and fluoroscopic images obtained during surgery are not taken into account seriously, but used just as a reference. This means that the success of surgery entirely depends on the surgeon's experience and skill.

In addition, artificial support structures (iron balls) are inserted into or attached to the patient's body, in order to align the coordinates of the surgical space to those of the image space.

After inserting or attaching the structures, the coordinates of the surgical space and those of the image space are obtained and aligned with each other. Such an additional process of insertion or attachment lengthens the surgery.

Although iron balls can be properly positioned when the surgical part is fully incised and exposed according to the conventional methods, artificial structures must be inserted or attached in advance when minimally invasive surgery needs to be performed in line with the current trends.

Generally, conventional industrial or medical robots use power transmission devices which have a high reduction ratio, such as motors, harmonic drives, or ball screws, for the purpose of automation and high positional precision. However, even when a surgeon needs to position a robot manually during surgery, he cannot do so in the case of a conventional robot, which is automatically driven by motors.

Therefore, it is requested to provide a robot which is not only automatically driven, but also manually positioned during surgery.

SUMMARY OF THE INVENTION

Accordingly, the present invention has been made to solve the above-mentioned problems occurring in the prior art, and an object of the present invention is to provide a computer-integrated surgery aid system for minimally invasive surgery, which combines a surgery planning system for planning minimally invasive surgery in the case of spinal surgery (e.g. spinal pedicle screw surgery, spinal endoscopy surgery, vertebroplasty, biopsy, scoliosis correction) with a surgery aid robot for performing surgery as planned, as well as a method for controlling the same.

Another object of the present invention is to provide a computer-integrated surgery aid system for minimally invasive surgery, which can establish an accurate three-dimensional surgery plan by using two sheets of two-dimensional images obtained through geometrical modeling of a patient in biplanar fluoroscopy, as well as a method for controlling the same.

Another object of the present invention is to provide a computer-integrated surgery aid system for minimally invasive surgery, which can establish an accurate surgery plan in real time by obtaining three-dimensional coordinates of desired points from a result of modeling in a biplanar fluoroscopy system through actual and image-based measurements and from the geometric relationship between the result and two sheets of fluoroscopic images, as well as a method for controlling the same.

Another object of the present invention is to provide a computer-integrated surgery aid system for minimally invasive surgery, which can obtain a three-dimensional coordinate of the human body by using fluoroscopic images so that it is suitable for a surgery planning system for minimally invasive surgery and which can relieve the patient of pain and the surgeon of labor, because no artificial structure needs to be inserted into or attached to the human body for surgery planning, as well as a method for controlling the same.

Another object of the present invention is to provide a computer-integrated surgery aid system for minimally invasive surgery, which has a robot operated either automatically or manually so that a surgery instrument can be accurately and easily positioned on the surgical part of a patient, the entry angle of the surgery instrument can be varied as desired for precise and stable surgery. Switch between automatic driving and manual operation of the robot arm is possible so that, even when the robot arm's driving device malfunctions due to unexpected accident, the robot arm can be manually operated for continuous surgery, as well as a method for controlling the same. Another object of the present invention is to provide a computer-integrated surgery aid system for minimally invasive surgery, which can efficiently support a surgery instrument, which is moved from a robot arm to a surgical part during surgery, so that the surgery instrument does not play in the lateral direction.

In order to accomplish these objects, a computer-integrated surgery aid system is provided for minimally invasive surgery using a computer and a surgery aid robot, the system including a frame having a ring shape; a plurality of radioactive generators positioned on an identical vertical surface of the frame at intervals of 90°, the radioactive generators irradiating X-ray signals to upper and lateral surfaces of a surgical object, respectively; a plurality of image pickups positioned on the frame while facing the radioactive generators, the image pickups receiving planar and lateral radioactive rays transmitted through the surgical object, respectively; a computer for receiving planar and lateral two-dimensional images of the surgical object from the image pickups and processing the two-dimensional images according to an algorithm so that three-dimensional position information of a surgical part is created; a monitor for displaying both two-dimensional images processed by the computer and an image corresponding to the three-dimensional position information; and a surgery aid robot for guiding a position and an entry angle of a surgical instrument according to a position of the surgical part with reference to data obtained from the computer, the surgery aid robot having a number of robot links connected to one another by joints, a surgical instrument support platform coupled to a guide arm corresponding to a distal robot arm, and a guide arm rotation means for rotating the guide arm so that the angle of the surgical instrument support platform is adjusted.

Specifically, model disks for measurement are fixedly positioned on a front end of first and second image pickups, respectively, reference points being marked on the model disks. The guide arm rotation means is a differential device for transmitting rotational force of a reduction motor positioned on a robot arm adjacent to the guide arm so that the guide arm is rotated axially and vertically.

The differential device includes a driving gear rotated by the driving force of the reduction motor; a pair of differential pinions engaging with the driving gear and rotating synchronously, the differential pinions being positioned on both sides of a differential shaft coaxial with the robot arm adjacent to the guide aim; and a differential side gear positioned on a shaft of the guide arm, both sides of the differential side gear engaging with the differential pinions, respectively. The differential device includes a pair of reduction motors and a pair of driving gears so that the differential pinions engage with respective driving gears and rotate accordingly.

The surgical instrument support platform has an instrument tool, and an instrument insertion hole is formed at the center of the instrument tool so that the surgical instrument is inserted into the instrument insertion hole and moved.

In accordance with another aspect of the present invention, provided is a computer-integrated surgery control method for minimally invasive surgery using a computer and a surgery aid robot, the method including the steps of (a) moving the surgery aid robot along a predetermined path and photographing the surgery aid robot so that the surgical space is aligned with the image coordinates; (b) positioning a surgical object on a surgical table and obtaining planar and lateral images of the surgical object; (c) finding a point corresponding to a surgical part and creating three-dimensional position information by the computer so that a surgery path is planned; (d) transmitting surgery path data to the surgery aid robot; and (e) guiding position and entry angle of a surgical instrument according to the position of the surgical part with reference to the surgery path data and aiding surgery by the surgery aid robot.

Specifically, step (a) includes the steps of fixedly setting model disks for measurement on planar and lateral image pickups for measurement of fluoroscopic images; irradiating radioactive rays in planar and lateral directions with the model disks being set and obtaining two-dimensional images in both directions; receiving both two-dimensional images and displaying the images in real time by the computer; rotating the images in a reverse direction by a rotational angle and displaying the images on a screen so that the rotational angle of the images measured via the model disks is compensated for; moving the surgery aid robot along a predetermined path, photographing the surgery aid robot, performing least square fitting by using the coordinates of an end point of the surgery aid robot, the coordinates resulting from photography, and aligning the surgical space with the image coordinates; and defining relationship between two coordinate systems by aligning three-dimensional coordinates of the surgery aid robot with three-dimensional coordinates of the images.

When the images are displayed on the screen, a total of four images are displayed, the four images including a planar image, a lateral image, and two corrected images. When the relationship between two sets of coordinates is specified by using the coordinates of the end point of the surgery aid robot and the coordinates being obtained from the planar and lateral images, the end point of the surgery aid robot is directly clicked and found by a user based on automatic movement of the surgery aid robot and an image reflecting the movement, and the point is used to perform a predetermined algorithm and specify the relationship between two sets of coordinates.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, a preferred embodiment of the present invention will be described with reference to the accompanying drawings. In the following description and drawings, the same reference numerals are used to designate the same or similar components, and so repetition of the description on the same or similar components will be omitted.

Figure 1:
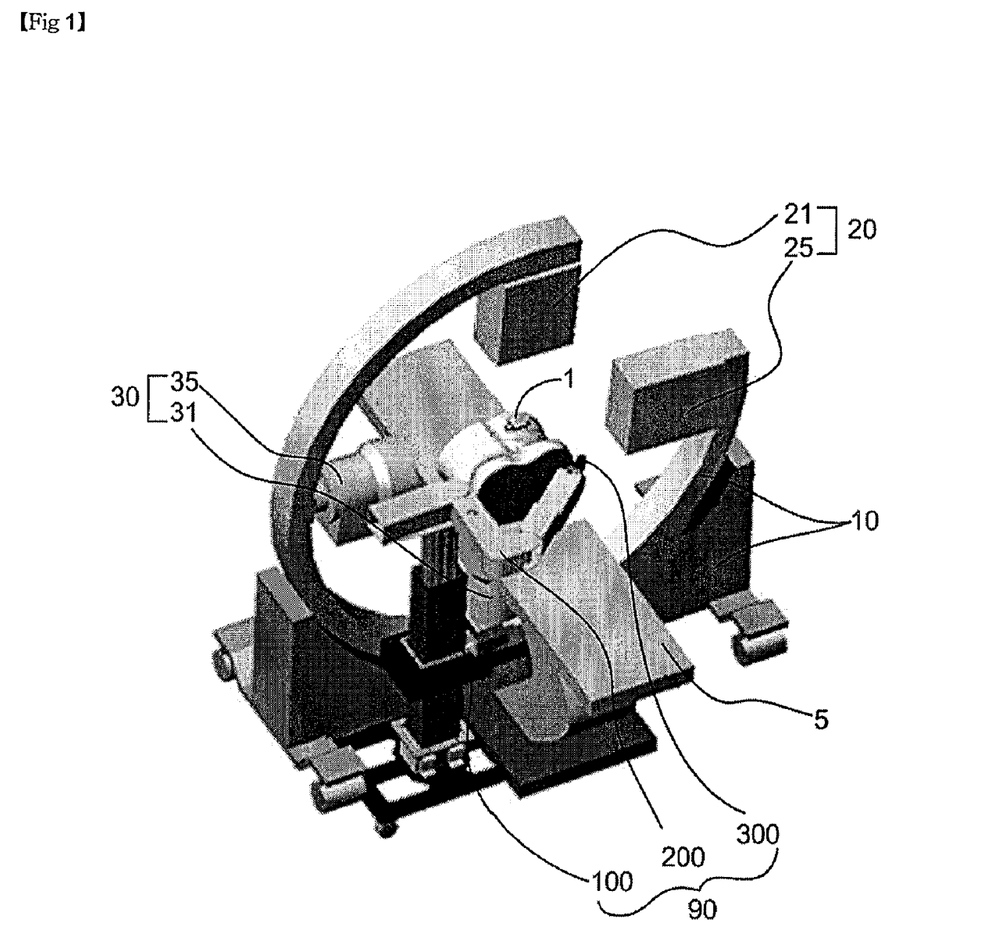
FIG. 1 is a conceptual diagram showing a computer-integrated surgery aid system according to the present invention.
Figure 2:
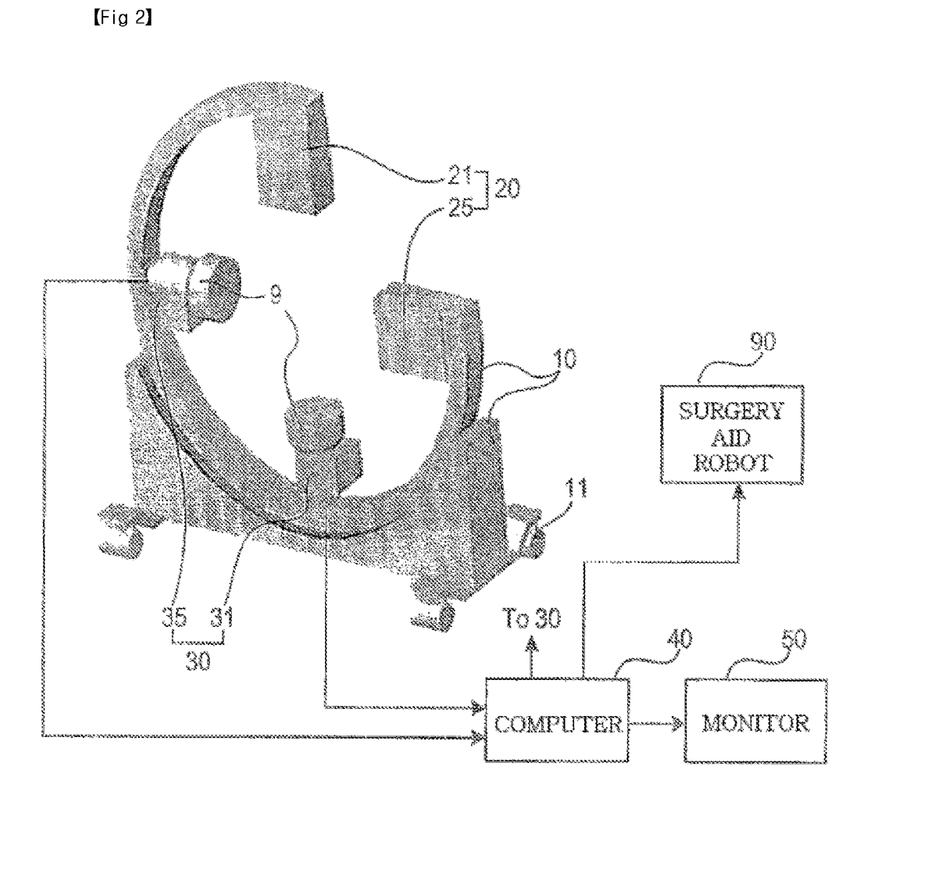
FIG. 2 shows a biplanar fluoroscopy system of the computer-integrated surgery aid system shown in FIG. 1, according to an embodiment of the present invention.

FIG. 1 is a conceptual diagram showing a computer-integrated surgery aid system according to the present invention, and FIG. 2 shows a biplanar fluoroscopy system of the computer-integrated surgery aid system shown in FIG. 1. As shown, the computer-integrated surgery aid system includes a frame 10, a radioactive generator 20, an image pickup 30, a computer 40, and a surgery aid robot 90.

The frame 10 has a plurality of radioactive generators 20; 21, 25 and a plurality of image pickups 30; 31, 35 positioned so as to face the radioactive generators on the same vertical surface of the frame 10 at an interval of 180°. Particularly, the radioactive generators 20 include first and second radioactive generators 21 and 25 arranged on the same vertical surface of the frame 10 at intervals of 90° so as to radiate X-ray signals toward the top and side of a surgical object 1. The image pickups 30 include first and second image pickups 31 and 35 arranged on the same vertical surface of the frame 10 at intervals of 90° while facing the radioactive generators 20, respectively, so as to pick up two-dimensional fluoroscopic images (i.e. planar and lateral images) of the surgical object 1.

Figure 3A:
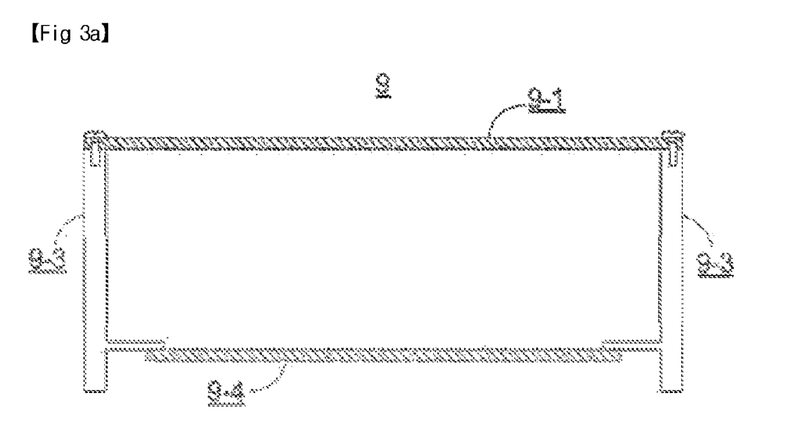
FIGS. 3a to 3c show model disks for measurement according to the present invention.
Figure 3B:
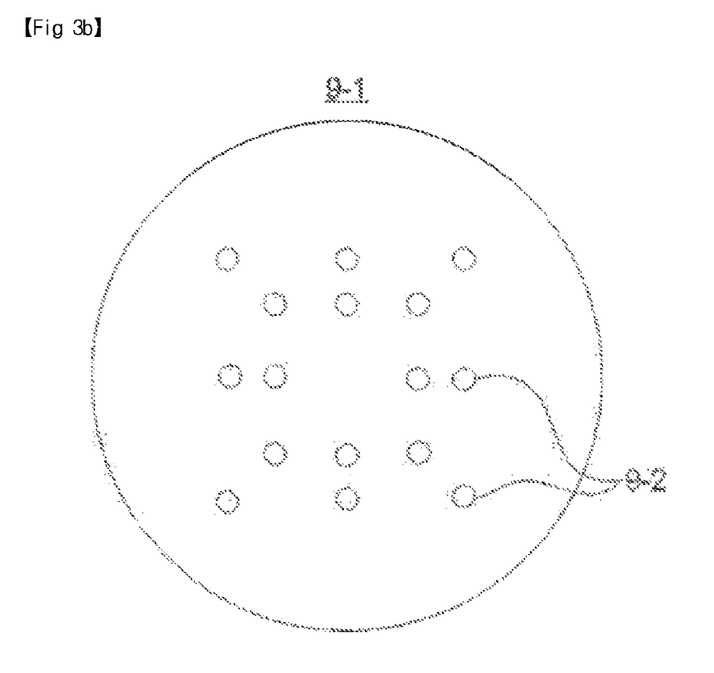
Figure 3C:
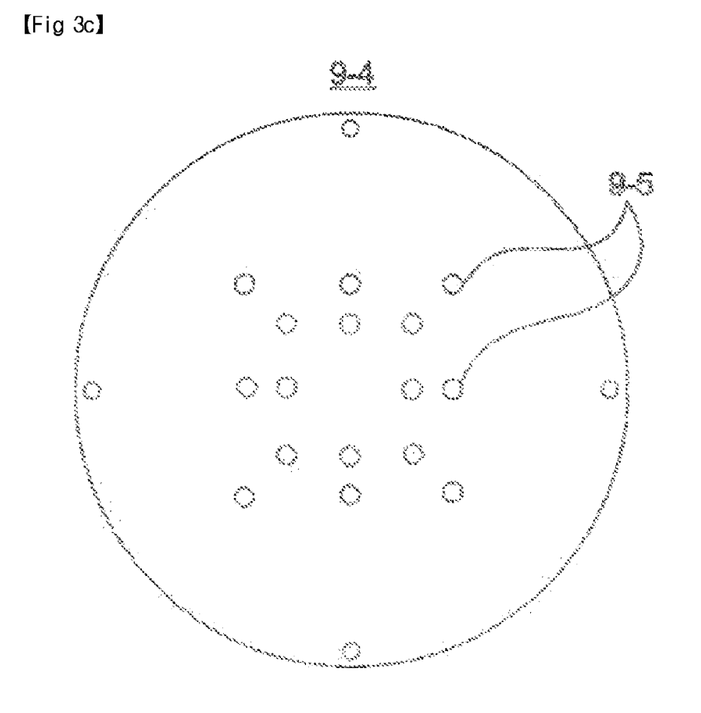

Model disks 9 for measurement are fixedly positioned on and protrude from the front surface of the first and second image pickups 31 and 35, respectively. The model disks 9 are made of a transparent material, as shown in FIGS. 3a to 3c, and include front and rear plates 9-1 and 9-4, which are spaced a distance by barriers 9-3. The front and rear plates 9-1 and 9-4 have measurement reference points 9-2 and 9-5 coordinated and marked thereon, respectively.

The computer 40 receives two-dimensional images (i.e. planar and lateral images) of the surgical object 1 from the first and second image pickups 31 and 35 and processes the images according to a predetermined algorithm so that the three-dimensional position information of the surgical part is created. The monitor 50 displays the two-dimensional images, which have been processed by the computer 40, as well as images regarding the three-dimensional position information. The surgery aid robot 90 positions a surgical instrument 300 and adjusts its entry angle with regard to the surgical part while making reference to data obtained from the computer 40.

The monitor 50 has function buttons 55 positioned on its lower end so that a user interface for adjusting displayed images is provided. The function buttons 55 include buttons for opening image files, correcting images, modifying and resetting three-dimensional space.

When the surgical object 1 is positioned on a surgical table 5, the radioactive generators 20 and image pickups 30 are used to obtain two sheets of two-dimensional images (i.e. planar and lateral images) of the surgical part.

These images are used to obtain three-dimensional position data of the surgical part, and the data is transmitted to the 6 degree-of-freedom surgery aid robot 90. Then, the robot 90 positions the surgical instrument 300 and adjusts its entry angle with regard to the surgical part while making reference to the data.

FIG. 2 shows the structure of a biplanar fluoroscopy system. The frame 10 has wheels 11 positioned on its lower end. The wheels 11 can be fixed to the ground so that the fluoroscopy device can be moved to a desired place and remain stationary.

For example, two X-Ray generators 21 and 25 and two X-ray receivers 31 and 35 are attached to the frame 10 of the biplanar fluoroscopy system at intervals of 90° so that two-dimensional images (i.e. planar and lateral images) of the surgical part are obtained and used to create three-dimensional position information.

According to the prior art, as disclosed in Korean Laid-open Patent Application No. 1998-7009294, C-Arm equipment must be operated so as to obtain biplanar fluoroscopy images of a surgical part, and two images are separately displayed and processed by two computers. However, according to the present invention, two images are obtained simultaneously and displayed by a single computer 40. In addition, no fiducial marker is used for coordinate alignment between the space, from which images are obtained by the equipment, and two fluoroscopy images.

Advantageously, this relieves the patient's pain resulting from insertion or attachment of a fiducial marker and the surgeon of corresponding labor.

As such, the present invention provides a surgery planning system conforming to the current trends toward minimally invasive surgery.

Figure 4:
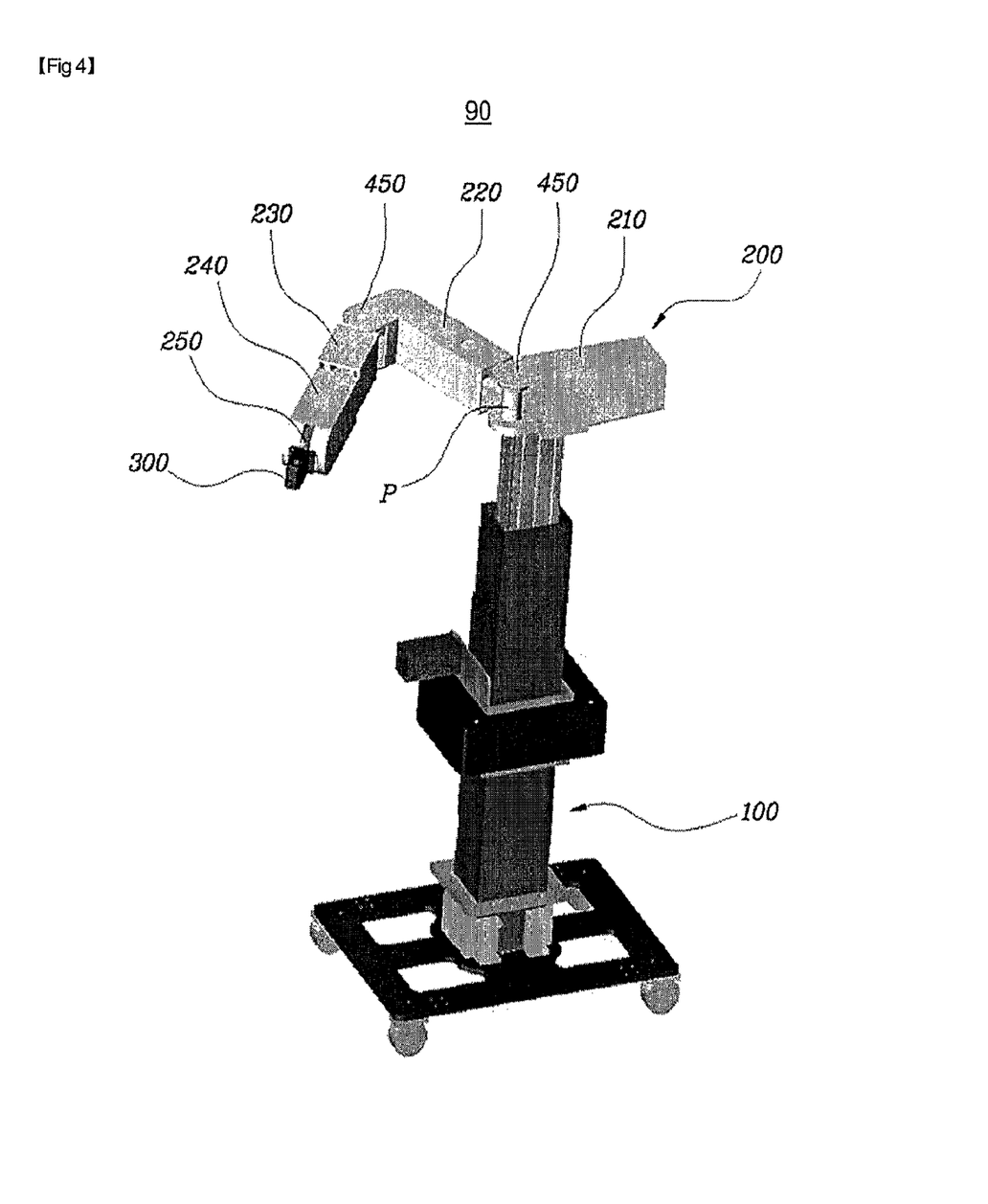
FIG. 4 is a perspective view showing a multiple degree-of-freedom surgery aid robot according to the present invention.
Figure 5:
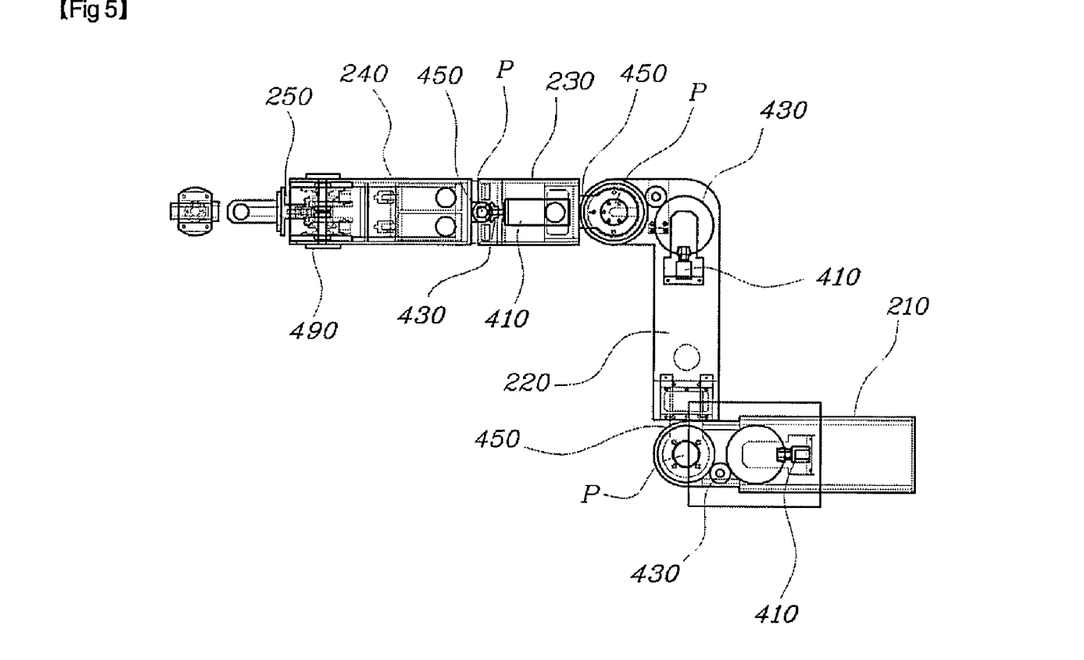
FIG. 5 is a top view showing a robot arm of the robot shown in FIG. 4, according to the present invention.
Figure 6:
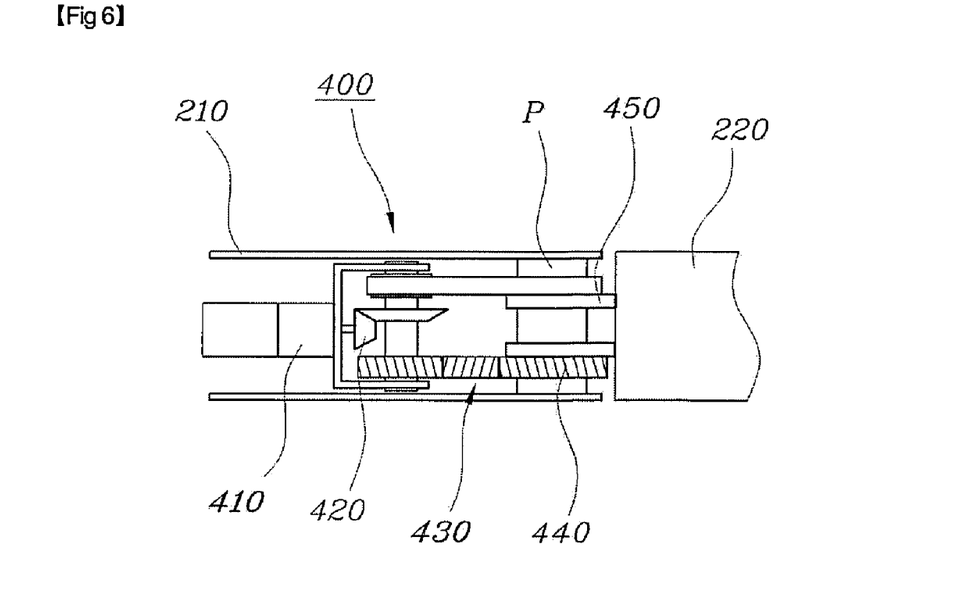
FIG. 6 is a longitudinal section view showing the robot-arm's rotation means of the robot shown in FIG. 4, according to the present invention.
Figure 7:
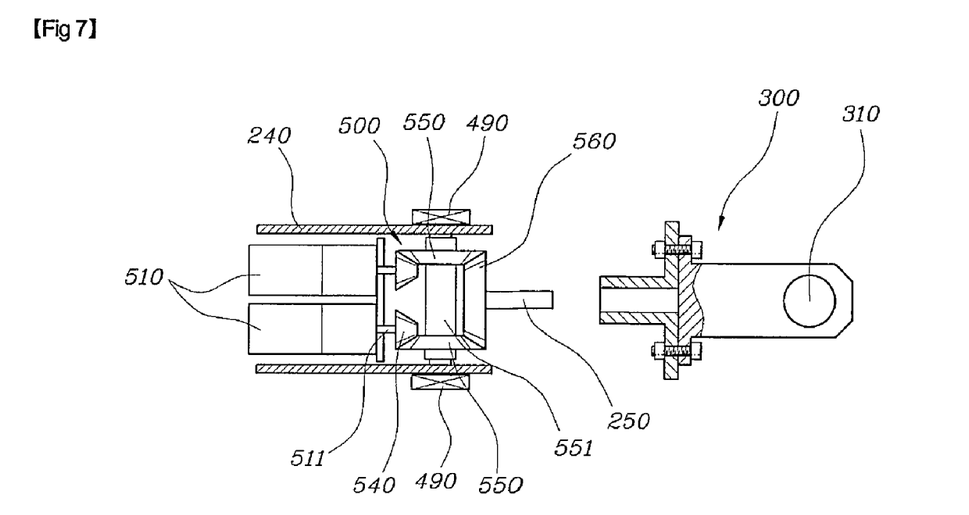
FIG. 7 is a transverse section view showing a guide arm rotation means of the robot shown in FIG. 4, according to the present invention.

FIG. 4 is a perspective view showing a multiple degree-of-freedom surgery aid robot according to the present invention. FIGS. 5 to 7 show in detail a robot arm, the robot arm's rotation means, and the guide arm's rotation means, respectively, according to an embodiment of the present invention.

Referring to FIG. 4, the surgery aid robot 90 includes a support 100; a number of robot arms 200 connected to one another via joints 260 and joint shafts P with one side of the robot arms 200 being supported on the support 100; a surgical instrument support platform 300 coupled to a guide arm 250, which corresponds to a distal one of the robot arms 200; and the guide arm's rotation means for rotating the guide arm 250 so that the angle of the surgical instrument support platform 300 can be adjusted.

The support 100 may be fixed to the ground so that stable operation of the robot arm 200 is guaranteed. Alternatively, the support 100 may be moved vertically by a lifting means, as shown in FIG. 4. However, the construction of the support 100 is not limited to that in the present invention, as long as it can sufficiently support the robot arms 200.

The robot arms 200 have sufficient (specifically, 5) degrees-of-freedom to accurately position the surgery instrument with regard to a surgical part of the patient without interfering with the surgeon's operation and surroundings of the operation room.

Referring to FIG. 5, a top view of the robot arms 200 is given. The robot arms 200 include a first robot link 210 mounted on top of the support 100; second, third, and fourth robot link 220, 230, and 240 connected to the first robot link 210, as well as to one another, by joints 260 and joint shafts P; and a guide arm 250 on which the surgical instrument support platform 300 is mounted.

At least, one of the robot links 200, preferably the second robot link 220 is bent at a predetermined angle. The bending angle of the second robot link 220 is 70-140°, preferably 90° (i.e. L-shaped configuration) so that one side of the second robot link 220 is parallel to the longitudinal direction of the surgical table 5. As used herein, the bending angle refers to the included angle at the bending point.

The surgery aid robot 90 may include a robot arm's rotation means 400 for rotating the robot arms 200. Referring to FIG. 6, the robot arm rotation means 400 includes a driving motor 410 positioned inside the first robot link 210 of the robot arms 200; a driving gear 420 positioned on a shaft of the driving motor 410; a transmission gear 430 consisting of a combination of at least one gear so that it engages with the driving gear 420 on one side and changes the rotational force; the following gear 440 positioned on the joint shaft P so as to engage with the other side of the transmission gear 430; and a pair of joints 450 connected to both sides of the joint shaft P, as well as to both sides of the second robot link 220 adjacent to the first robot link 210, respectively.

It is to be noted that the rotation means 400, which is positioned on the first robot link 210 and one side of the second robot link 220, is similarly constructed on the other side of the second robot link 220 and one side of the third robot link 230, as well as on the other side of the third robot link 230 and one side of the fourth robot link 240.

In addition, the construction of the transmission gear is not limited to that in the present invention, and various combinations of gears may be used to change the rotational force as desired and generate desired rotational force in the axial direction, as well as in the longitudinal and transverse directions. Those skilled in the art can easily implement the robot arm rotation means 400 by using any equivalently substitutable rotation means.

Referring to FIG. 7, the guide arm's rotation means includes a differential device 500 for transmitting the rotational force from a reduction motor 510, which is positioned on the fourth robot link 240 adjoining the guide arm 250, so that the guide arm 250 is rotated axially and vertically.

The differential device 500 includes a driving gear 540 rotated by driving force from the reduction motor 510; a pair of differential pinions 550 positioned on both sides of a differential shaft 551, which is coaxial with the fourth robot link 240 adjoining the guide arm 250, so that they engage with the driving gear 540 and rotate synchronously; and a differential side gear 560 positioned on a shaft of the guide arm 250 so that both sides of the differential side gear 560 engage with both sides of the differential pinions 550, respectively. As such, the differential device 500 transmits a rotational force from the reduction motor 510 to the guide arm 250.

Preferably, a pair of reduction motors 510 and a pair of driving gears 540 are provided so that the differential pinions 550 engage with respective driving gears 540 and rotate separately.

Figure 8:
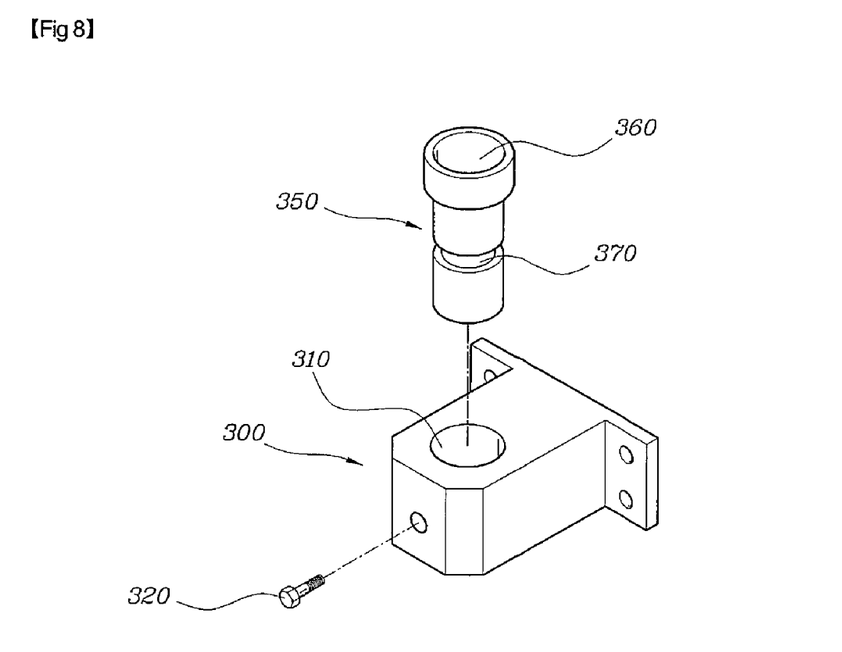
FIG. 8 shows a surgery instrument support platform and an instrument tool according to the present invention.

Referring to FIG. 8, an instrument tool 350 is adapted to be fixedly inserted into the surgical instrument support platform 300. The instrument tool 350 has a cylindrical shape with an instrument insertion hole 360 formed thereon so that a surgical instrument can be inserted therein. At least one line of groove 370 is formed along the outer periphery of the instrument tool 350 at a different level.

Preferably, the surgical instrument support platform 300 is provided with a fastener 320, which is forced against the groove 370, in order to fix the instrument tool 350 to the surgical instrument support platform 300.

In summary, the computer-integrated surgery aid system for minimally invasive surgery, as shown in FIG. 1, combines a surgery planning system 10-50, which is adapted to plan surgery in such a manner that the part to be incised during surgery is minimized, with a surgery aid robot 90 for performing operation as planned.

As used herein, the surgery planning system 10-50 refers to a system for calculating internal parameters of the biplanar fluoroscopy system used during surgery, modeling the imaging system based on calculated values, and calculating three-dimensional coordinates from two sheets of two-dimensional images. The surgery aid robot 90 refers to a scalar-type 6 degree-of-freedom robot designed and fabricated so as to perform a desired surgery based on the plan established by the surgery planning system.

The operation of the surgery planning system and the surgery system according to the present invention, which are constructed as above, will now be described.

Figure 9:
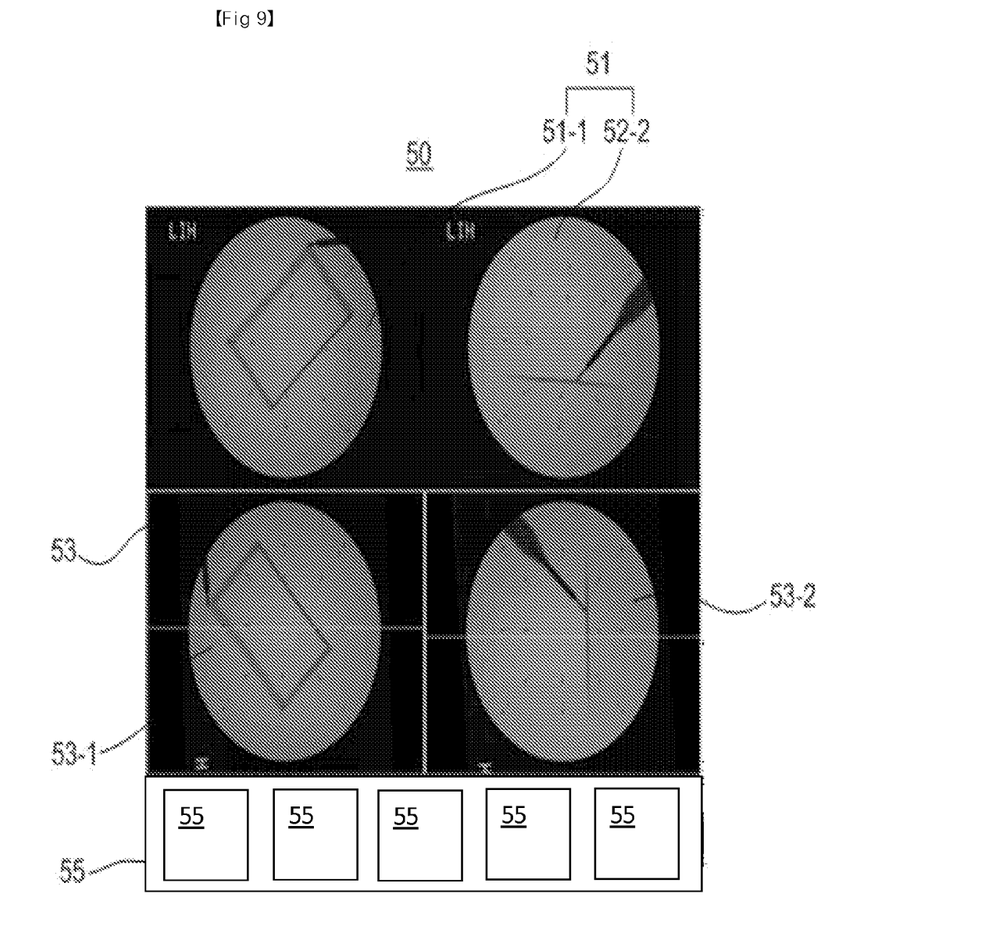
FIG. 9 shows the user interface environment of a surgery planning system according to the present invention.

FIG. 9 shows biplanar images obtained by the biplanar fluoroscopy system shown in FIG. 2, as well as the user interface environment. In particular, the monitor 50 displays images obtained by a plurality of radioactive generators 20 and image pickups 30.

Two images 51; 51-1, 51-2 on the upper screen of the monitor 50 are given by displaying images obtained by the image pickups 30 in real time, and two underlying images 53; 53-1, 53-2 are given to compensate for the rotational angle of the measured images by rotating them in the opposite direction as much as that angle.

Reference points marked on the screen correspond to reference points of the model disks 9, which are fixedly placed on the front surface of the first and second image pickups 31 and 35, respectively.

Among the displayed images, two underlying images 53 are used for all necessary processes, including alignment of spatial coordinates with image coordinates and surgical path planning.

These functions are selected and performed by means of the function buttons 55 of the user interface environment on the lower end of the screen.

Based on images obtained in the above procedure, three-dimensional coordinates are calculated according to an algorithm stored in the computer 40, so that three-dimensional position coordinates of the surgical part are determined. Upon receiving position control signals, the surgery aid robot 90 functions so as to approach the surgical part based on coordinate control signals.

Figure 10:
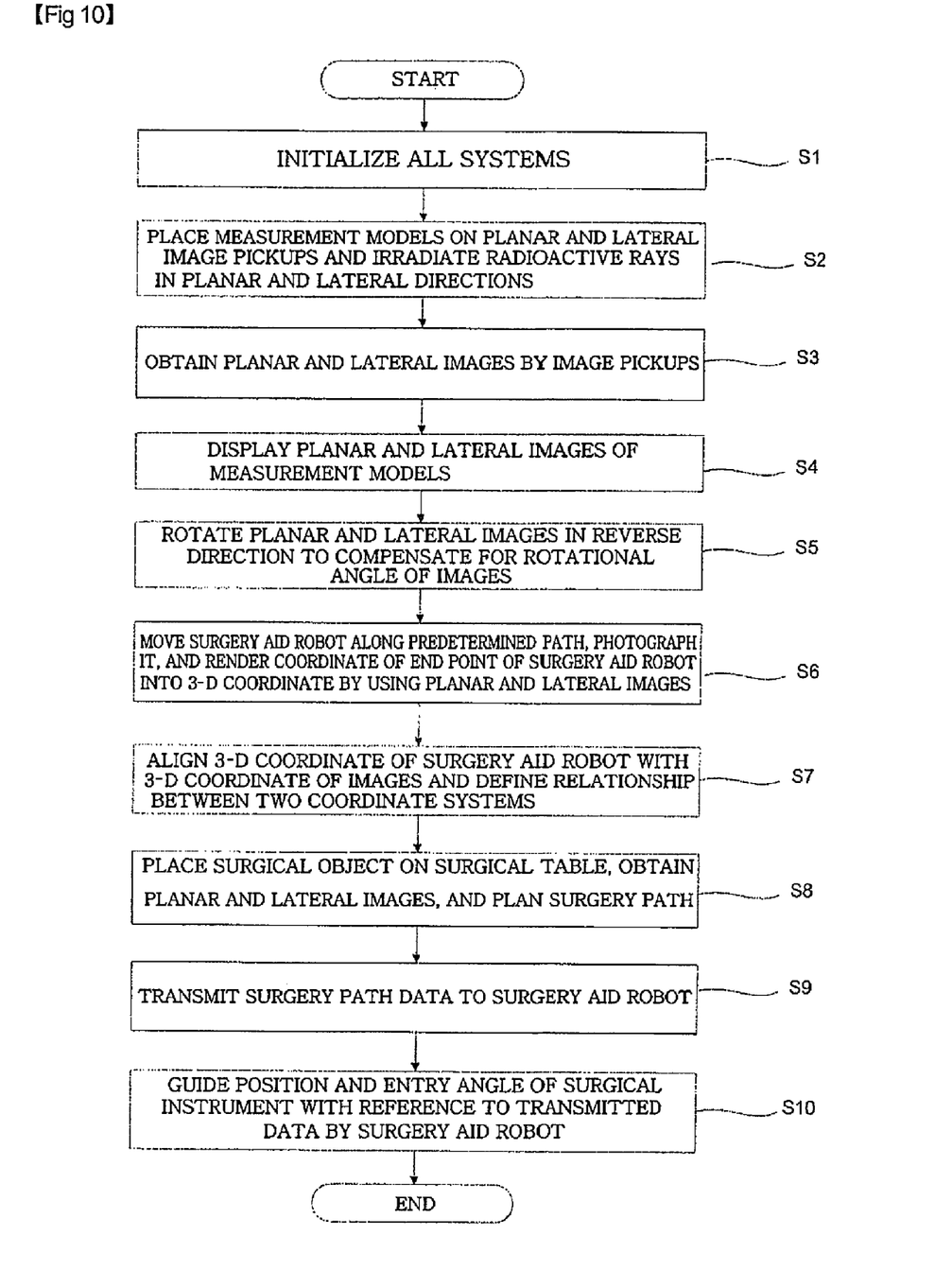
FIG. 10 is a flowchart showing a method for establishing a surgery plan by using a computer and a surgery aid robot according to an embodiment of the present invention.

A method for establishing a surgery plan by using the computer 40 and the surgery aid robot 90, which are constructed as above, will now be described with reference to FIG. 10, which shows a flowchart of the method.

After the model disks 9 for measurement are fixedly placed on the front surface of the first and second image pickups 31 and 35, respectively, the radioactive generators 20, the image pickups 30, the computer 40, and the surgery aid robot 90 are initialized for measurement of fluoroscopic images (S1).

The computer 40 controls the first and second radioactive generators 21 and 25 so as to irradiate radioactive rays in the planar and lateral directions in the absence of the surgical object 1. Then, the first and second image pickups 31 and 35 pick up biplanar images, i.e. planar and lateral images (S2, S3).

Upon receiving two sheets of two-dimensional images from the image pickups 30, the computer 40 properly processes the planar and lateral images and displays them on the upper screen of the monitor 50, as shown in FIG. 4 (S4).

In order to compensate for the rotational angle of the images, which have been measured via the model disks 9, the computer 40 rotates the images in the opposite direction by a predetermined angle (e.g. 90°) and displays them on the screen as shown in FIG. 8 (S5).

The computer 40 controls the surgery aid robot 90 and moves it along a predetermined path, so that it is photographed by the radioactive generators 20 and the image pickups 30 while being on the move. Based on the coordinate of the end point 300 of the surgery aid robot 90, which results from the photography, least square fitting is performed so as to obtain a surgical path in a three-dimensional coordinate system (S6).

The resultant traveling path of the surgery aid robot 90 and the surgical space are aligned with the coordinates of the planar and lateral images. Based on the alignment, coincidents points between both images are defined so that the coordinate of the biplanar fluoroscopy system 10-40 automatically coincide with those of the surgery aid robot 90 (S7). The monitor 50 displays the planar and lateral images, as well as their corrected images (i.e. a total of 4 images). When the relationship between both coordinates is to be defined by using the planar and lateral images of the surgical object 1 and the coordinate of the end point 300 of the surgery aid robot 90, the user manually clicks and traces the end point 300 of the surgery aid robot 90 based on the automatic movement of the surgery aid robot 90 and images reflecting that movement. These points are used to perform a predetermined algorithm and define the relationship between both sets of coordinates.

The surgical object 1 is placed on the surgical table, and planar and lateral images of the surgical part are obtained by using the first and second radioactive generators 21 and 25 and the first and second image pickups 31 and 35. The images are rendered in a three-dimensional coordinate system, and a surgery plan is established (S8).

Thereafter, two steps are performed. In the first step, if a point of one of the two-dimensional images (i.e. planar and lateral images) is clicked, a corresponding line is indicated on the other image. As the mouse is moved, points on that line are highlighted so that desired points can be selected from both images. In the second step, an entry point and a target point are designated and a corresponding path is displayed.

The entry and target points determined in the above steps are used as information regarding a surgical path for controlling the robot.

Figure 11:
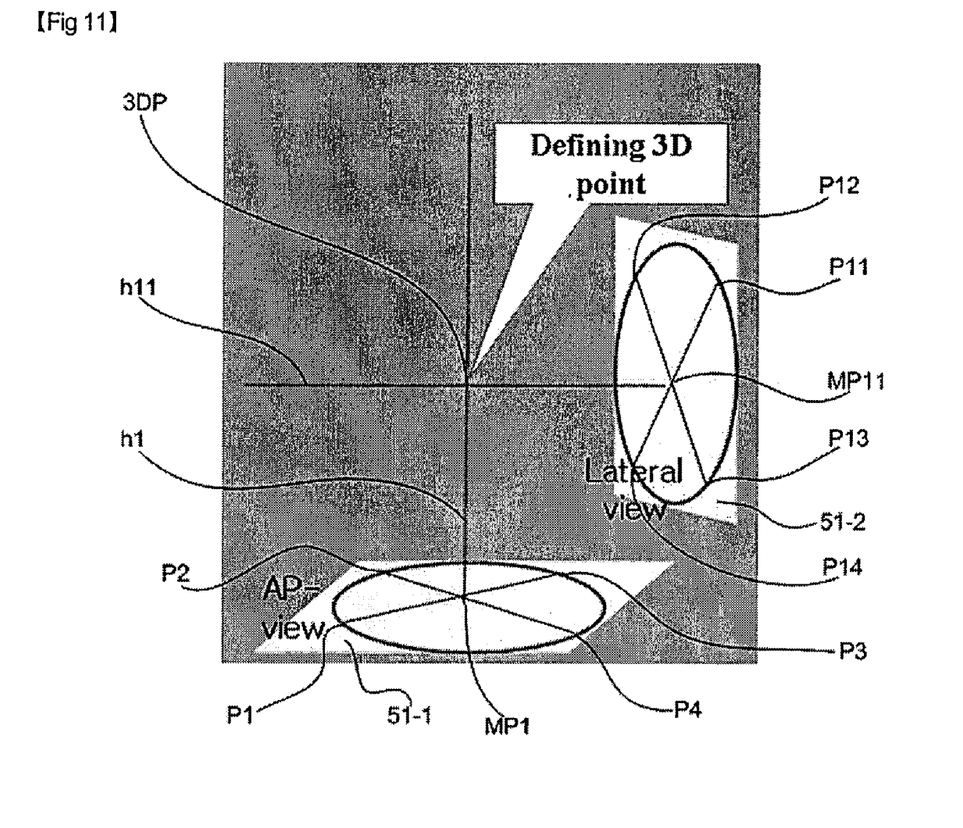
FIG. 11 is a graph showing a method for obtaining mid points of biplanar fluoroscopic images in a spatial coordinate system according to the present invention.

An algorithm for aligning the coordinates of the planar image with those of the lateral image (i.e. mid point calculation based on spatial coordinates) will now be described with reference to FIG. 11.

In order to obtain spatial coordinates, the computer 40 goes through the following steps.

(1) Normal vectors and mid points MP1 and MP2 of both planes 51-1 and 51-2 are calculated. It is assumed that two segments used for the calculation intersect with each other.

(2) Two lines h1 and h11 are obtained from the normal vectors and mid points calculated in step (1).

(3) An intersection point, 3D point or 3Dp, between both lines h1 and h11 is calculated.

(4) When both lines h1 and h11 are in a skew position, a point 3Dp is located where they are closest to each other.

The normal vectors and mid points of both planes 51-1 and 51-2 will now be considered with reference to a planar image AP-VIEW.

Assuming that four points P1(x1,y1,z1), P2(x2,y2,z2), P3(x3,y3,z3), and P4(x4,y4,z4) are on a circle on the plane 51-1, its plane equation is defined by equation (1) below.

$$aX+bY+cZ+d=0 \qquad (1)$$

Taking 1 for d, equation (1) is modified into equation (2) below.

$$aX+bY+cZ=-1 \qquad (2)$$

Substitution of each point gives equation (3) below.

$$\begin{pmatrix} ax1+by1+cz1=-1 \\ ax2+by2+cz2=-1 \\ ax3+by3+cz3=-1 \\ ax4+by4+cz4=-1 \end{pmatrix} \qquad (3)$$

Using matrices, equation (3) is modified into the equation (4) below.

$$\begin{pmatrix} x1 & y1 & z1 \\ x2 & y2 & z2 \\ x3 & y3 & z3 \\ x4 & y4 & z4 \end{pmatrix} \begin{pmatrix} a1 \\ b2 \\ c1 \end{pmatrix} = \begin{pmatrix} -1 \\ -1 \\ -1 \\ -1 \end{pmatrix} \qquad (4)$$

Or Xa=−1

Wherein, a=$(a_i,b_i,c_i)$ (i=1, 2, 3, 4)

Since this is an indeterminate equation, equation (4) is separated into four matrices by using (3*3) matrix combination, as defined by equation (5) below.

$$\begin{pmatrix} x1 & y1 & z1 \\ x2 & y2 & z2 \\ x3 & y3 & z3 \end{pmatrix}, \begin{pmatrix} x1 & y1 & z1 \\ x2 & y2 & z2 \\ x4 & y4 & z4 \end{pmatrix}, \begin{pmatrix} x1 & y1 & z1 \\ x3 & y3 & z3 \\ x4 & y4 & z4 \end{pmatrix}, \begin{pmatrix} x2 & y2 & z2 \\ x3 & y3 & z3 \\ x4 & y4 & z4 \end{pmatrix} \qquad (5)$$

For convenience, four matrices in equation (5) are termed X1, X2, X3, and X4, respectively, and the notation Xa=−1 of equation (4) is used. This gives equation (6) below.

$X1*a=-1$ $X2*a=-1\times$ $X3*a=-1$ $$X4*a=-1 \qquad (6)$$

Resultant values are $(a_i,b_i,c_i)$ (i=1, 2, 3, 4).

Then, normal vectors on the planar image AP-VIEW are defined by equation (7) below.

$A1=(a1+a2+a3+a4)/4$ $B1=(b1+b2+b3+b4)/4$ $$C1=(c1+c2+c3+c4)/4 \qquad (7)$$

Wherein, respective values of (a1+a2+a3+a4), (b1+b2+b3+b4), (c1+c2+c3+c4) are substantially identical. However, they have been averaged for exactness.

Normal vectors A2, B2, and C2 of the lateral image LATERAL-VIEW are obtained similarly.

Regarding the lines h1 and h11, the mid point MP1 of the planar image AP-VIEW is (X1,Y1,Z1), and the normal vector thereof is (A1,B1,C1).

The mid point MP11 of the lateral image LATERAL-VIEW is (X2,Y2,Z2), and the normal vector thereof is (A2, B2,C2).

The normal lines of the planar and lateral images AP-VIEW and LATERAL-VIEW are defined by equations (8a) and (8b) below.

$$\frac{X-X1}{A1}=\frac{Y-Y1}{B1}=\frac{Z-Z1}{C1}=t \qquad (8a)$$

$$\frac{X-X2}{A2}=\frac{Y-Y2}{B2}=\frac{Z-Z2}{C2}=s \qquad (8b)$$

Arranging equations (8a) and (8b) in terms of X, Y, and Z, they are modified into equations (9) and (10) below.

$$\begin{pmatrix} X=A1*t+X1 \\ Y=B1*t+Y1 \\ Z=C1*T+Z1 \end{pmatrix} \qquad (9)$$

$$\begin{pmatrix} X=A2*s+X2 \\ Y=B2*s+Y2 \\ Z=C2*s+Z2 \end{pmatrix} \qquad (10)$$

Solution of the intersection point 3Dp between both lines h1 and h11 gives equation (11) below, assuming that both above equations are identical.

$A1*t+A1=A2*s+X2$ $B1*t+Y1=B2*s+Y2$ $C1*t+Z1=C2*s+Z2$ $$A1*t - A2*s = X2 - X1$$

$$\Rightarrow B1*t - B2*s = Y2 - Y1$$

$$C1*t - C2*s = Z2 - Z1$$

$$\Rightarrow \begin{pmatrix} A1 - A2 \\ B1 - B2 \\ C1 - C2 \end{pmatrix} \begin{pmatrix} t \\ s \end{pmatrix} = \begin{pmatrix} X2 - X1 \\ Y2 - Y1 \\ Z2 - Z1 \end{pmatrix} \quad (11)$$

After calculating t and s from equation (11), they are substituted into equations (8a) and (8b). As a result, the spatial intersection point 3Dp (x, y, z) is obtained.

A procedure for establishing a plan of minimally invasive surgery according to the present invention will now be described briefly.

A surgical object 1 (e.g. measurement model or human body) is used to calculate the inner parameters of biplanar fluoroscopic images and model the imaging equipment 20 and 30. This compensates for any rotational angle of the imaging equipment and guarantees accurate three-dimensional display of both images, which are two-dimensional, on the imaging equipment.

The surgery aid robot 90 is moved along a predetermined path without using any artificial structure and is photographed so that the surgical space is aligned with the coordinates of the images. The result of the alignment is used to find coincident points between both images and render them in a three-dimensional coordinate system. Entry and target points can be designated in this process.

After creating surgical path data in this manner, the computer 40 transmits it to the surgery aid robot 90 via a TCP/IP network (S9). Based on the surgical path data regarding coordinates from the computer 40, the surgery aid robot 90 controls the operation of the robot arms in accordance with the location of the surgical part. Particularly, the surgery aid robot 90 positions the surgery instrument and adjusts its entry angle so that the surgeon can perform surgery as guided by the robot.

The surgery aid robot 90 is adapted to direct the surgical instrument support platform 300, which is coupled to the guide arm 250, at various angles when the guide arm 250 rotates axially or vertically.

Particularly, the driving motor 410 is supplied with external power under the control of the computer 40 and rotates the second, third, and fourth robot links 220, 230, and 240 at an angle relative to the first robot link 210. In addition, the reduction motor 510 is driven to rotate the guide arm 250 at an angle. As such, the surgical instrument support platform 300 is positioned in accordance with the coordinates of the surgical part specified by the computer 40.

The surgeon can confirm whether the surgical instrument support platform 300 and the surgical instrument are correctly positioned with regard to the surgical part by watching image data transmitted from the image pickups 30 and displayed on the monitor 50.

The joint shafts P, which connect the first to fourth robot links 200, 210, 220, and 230 to one another, but not the guide arm 250, may be rotated by separate motors and gear connection structures, so that the robot arms 200 can be automatically operated by the motors under the control of the computer 40.

A means for sensing rotational angle may be additionally provided so that the range of rotation of the reduction motor 510 is detected and the resulting signal is transmitted to the computer 40. As the means for sensing rotational angle, an encoder sensor 490 capable of detecting the amount of rotation of the reduction motor 510 is preferably used.

The rotational angle of the guide arm 250, which has been sensed by the encoder sensor 490, is fed back according to an algorithm stored in the computer 40 so that the range of rotation of the reduction motor 510 is controlled. As a result, the surgical instrument support platform 300 is accurately positioned with regard to the surgical part.

When the position of the surgical instrument support platform 300 is made to coincide with coordinate values calculated by the computer 40 in the above procedure, the surgeon incises the patient's skin minimally and mounts a surgical instrument onto the surgical instrument support platform 300. Then, he can perform necessary surgery with the aid of the surgery aid robot.

The surgery aid robot according to the present invention guarantees safety and precision of spinal surgery, which requires a high degree of precision.

After the operation is over, the surgeon sutures the incision and presses an operation button (not shown) so that the surgery aid robot returns to the original state. In this case, the fourth robot link 240 and the guide arm 250 are rotated and fastened against the second robot link 220, which has an L-shaped configuration. This efficiently reduces the space occupied by the robot arms 200.

Although the robot arms 200 are driven automatically by driving devices as mentioned above, they may also be operated manually when, for example, their driving devices malfunction due to an unexpected accident or when power supply to the driving devices is interrupted for manual operation.

In summary, the multiple degree-of-freedom robot according to the present invention has a small range of displacement of the entire robot arms 200, due to the strong structural properties of the second robot arm 220. Therefore, the robot can accurately position the surgical instrument support platform with regard to the surgical part without interfering with other surgical instruments or the surgeon. In addition, the surgical instrument support platform 300 can be directed at the tilt angle of the spine. Particularly, the robot avoids vertical movement when screw holes are made on the spine. As such, the robot relieves the patient of the burden of surgery and guarantees precise and safe surgery. In short, the present invention has made a breakthrough in the medical robot industry.

As mentioned above, the present invention is advantageous in that an accurate three-dimensional surgery plan is established by using two sheets of two-dimensional images obtained through geometrical modeling of a patient in biplanar fluoroscopy, in the case of spinal surgery (e.g. spinal pedicle screw surgery, spinal endoscopy surgery, vertebroplasty, spinal tissue inspection, scoliosis correction).

In addition, an accurate surgery plan is established in real time by obtaining three-dimensional coordinates of desired points from a result of modeling in a biplanar fluoroscopy system through actual and image-based measurements and from geometric relationship between the result and two sheets of fluoroscopic images. Furthermore, three-dimensional coordinates of the human body are obtained by using fluoroscopic images so that the present invention is suitable for a surgery planning system for minimally invasive surgery. The present invention also relieves the patient of pain and the surgeon of labor, because no artificial structure needs to be inserted into or attached to the human body for surgery planning.

Due to the operational structure of the robot arms and the shape of the bent second robot arm, the inventive surgery aid robot can be operated in a narrower space than in the case of conventional robots. Therefore, the inventive surgery aid robot can prevent medical accidents resulting from interference with other surgical instruments. In addition, the surgeon is provided with a larger surgical space. This improves the safety of surgery.

The surgical instrument can be accurately positioned at the tilt angle of the spine by adjusting the angle of the surgical instrument support platform, on which the surgical instrument is mounted. An instrument tool is used to properly support the surgical instrument, which is moved from the robot arms to the surgical part during surgery, and is also prevents the surgical instrument from operating in the lateral direction. This improves the precision and safety of surgery.

The invented robot is adapted to be operated manually, as well as driven automatically. Therefore, even when the driving devices of the robot arms malfunction due to an unexpected accident, the robot can be operated manually so that surgery can be performed without stopping. This prevents any medical accident resulting from erroneous operation of the robot.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A computer-integrated surgery aid system for minimally invasive surgery using a computer and a surgery aid robot, the system comprising:
   a frame having a ring shape;
   a plurality of radioactive generators positioned on an identical vertical surface of the frame at intervals of 90°, the radioactive generators irradiating X-ray signals through a surgical space, as well as to upper and lateral surfaces of a surgical object, respectively, when the surgical object is placed within the surgical space;
   a plurality of image pickups positioned on the frame while facing the radioactive generators, respectively, the image pickups receiving planar and lateral radioactive rays transmitted through the surgical space, as well as through the surgical object when the surgical object is within the surgical space;
   a surgery aid robot;
   a computer for receiving planar and lateral two-dimensional images of the surgical space alone, as well as for receiving planar and lateral two-dimensional images of the surgical space when the surgery aid robot is moved along a predetermined path within the surgical space to obtain image coordinates of the surgery aid robot,
   wherein the computer performs least square fitting using the image coordinates to align the surgical aid robot directly with the surgical space, and
   wherein the computer also receives planar and lateral two-dimensional images of the surgical object from the image pickups when the surgical object is placed within the surgical space, and the computer processes the two-dimensional images of the surgical object according to an algorithm so that three-dimensional position information of the surgical object is created with respect to the alignment between the surgical space and the surgery aid robot;
   a monitor for displaying both two-dimensional images processed by the computer and an image corresponding to the three-dimensional position information;
   the surgery aid robot for guiding the position and entry angle of a surgical instrument according to a position of the surgical object with reference to data obtained from the computer, the surgery aid robot having a plurality of robot links connected to one another by joints, a surgical instrument support platform coupled to a guide arm, and a guide arm rotational means for rotating the guide arm so that an angle of the surgical instrument support platform is adjustable,
   wherein the guide arm's rotational means is a differential device for transmitting rotational force of a reduction motor positioned on a robot arm adjacent to the guide arm so that the guide arm is rotated axially and vertically, and
   wherein the differential device comprises a driving gear rotated by the driving force of the reduction motor; a pair of differential pinions engaging with the driving gear and rotating synchronously, the differential pinions being positioned on both sides of a differential shaft coaxial with the robot arm adjacent to the guide arm; and a differential side gear positioned on a shaft of the guide arm, both sides of the differential side gear engaging with the differential pinions, respectively.

2. The system as claimed in claim 1, further comprising:
   model disks for measurement, the model disks being fixedly positioned on an end of a first image pickup of the plurality of image pickups that receives the lateral radioactive rays and on an end of a second image pickup of the plurality of image pickups that receives the planar radioactive rays, wherein each of the model disks comprises reference points marked on the model disks, and
   wherein each of the model disks further comprises transparent front and rear plates that are spaced apart a predetermined distance by a barrier, the front plate being larger in diameter than the rear plate and each of the front and rear plates having respective reference points marked thereon for facilitating measurement of the lateral and planar images and a rotational angle of the images.

3. The system as claimed in claim 1, wherein the differential device comprises a pair of reduction motors and a pair of driving gears so that the differential pinions engage with the respective driving gears and rotate accordingly.

4. The system as claimed in claim 1, wherein the surgical instrument support table has an instrument tool, and an instrument insertion hole is formed at a center of the instrument tool so that the surgical instrument is inserted into the instrument insertion hole and moved.

5. A computer-integrated surgery control method for minimally invasive surgery using a computer and a surgery aid robot, the method comprising the steps of:
   (a) obtaining biplanar images of a surgical space absent a surgical object;
   (b) subsequently moving the surgery aid robot along a predetermined path within the surgical space and photographing the surgery aid robot as the surgery aid robot moves within the surgical space to obtain image coordinates of the surgery aid robot within the surgical space;
   (c) aligning the biplanar images of the surgical space with the image coordinates of the surgery aid robot within the surgical space by defining a coordinate relationship between the biplanar images and the image coordinates;
   (d) thereafter positioning a surgical object within the surgical space and obtaining planar and lateral images of the surgical object;
   (e) selecting a point corresponding to a surgical part of the surgical object and creating three-dimensional position information by the computer so that a surgery path is planned with respect to the point;

(f) transmitting surgery path data to the surgery aid robot; and (g) guiding position and entry angle of a surgical instrument according to the position of the surgical part with reference to the surgery path data by the surgery robot, wherein each of a first three robot links of the plurality of robot links comprises a rotational means, the rotational means comprising a reduction motor and a differential device for transmitting rotational force of the reduction motor to a sequential robot link, the rotational means being positioned such that each of the plurality of robot links can be rotated axially and vertically.

6. The method as claimed in claim 5, wherein the method further comprises the steps of:

fixedly setting model disks for measurement on planar and lateral image pickups for measurement of fluoroscopic images;

irradiating radioactive rays in planar and lateral directions with the model disks being set and obtaining two-dimensional images in both directions;

receiving both two-dimensional images and displaying the images in real time with the computer;

rotating the images in a reverse direction by a rotational angle and displaying the images on a screen so that the rotational angle of the images measured via the model disks is compensated for;

moving the surgery aid robot along a predetermined path, photographing the surgery aid robot, performing least square fitting by using the coordinates of an end point of the surgery aid robot, the coordinates resulting from photography, and aligning the surgical space with the image coordinates; and defining a relationship between two coordinate systems by aligning the three-dimensional coordinates of the surgery aid robot with the three-dimensional coordinates of the images.

7. The method as claimed in claim 6, wherein the displaying the images on a screen further comprises displaying a total of four images, the four images including a planar image, a lateral image, and two corrected images.

8. The method as claimed in claim 6, wherein, when the relationship between two sets of coordinates is specified by using the coordinates of the end point of the surgery aid robot and the coordinates being obtained from the planar and lateral images, the end point of the surgery aid robot is directly clicked and found by a user based on automatic movement of the surgery aid robot and an image reflecting the movement, and the point is used to perform a predetermined algorithm and to specify the relationship between the two sets of coordinates.

9. The system as claimed in claim 1, wherein at least a second robot link of the plurality of robot links has a manufactured bend therein to minimize the size of the whole robot arm; and wherein the manufactured bend is between 70 and 120 degrees.

10. The system as claimed in claim 9, wherein the manufactured bend is 90 degrees.

* * * * *